United States Patent [19]
Cocanour, III

[11] Patent Number: 5,517,237
[45] Date of Patent: May 14, 1996

[54] VIDEO PHOTOMETRIC COLOR SYSTEM FOR PROCESSING COLOR SPECIFIC STREAMS

[75] Inventor: John B. Cocanour, III, Sandy, Utah

[73] Assignee: The Unied States of America as represented by the Secretary of the Interior, Washington, D.C.

[21] Appl. No.: 294,125

[22] Filed: Aug. 22, 1994

[51] Int. Cl.⁶ .................................................. H04N 17/02
[52] U.S. Cl. ........................... 348/189; 348/179; 348/649; 266/80; 73/61.42; 73/23.2
[58] Field of Search ..................................... 348/645, 647, 348/649, 657, 659, 175, 187, 179, 180, 181; 266/80, 99; 73/61.42, 61.69, 64.41, 23.2, DIG. 11, 19.07, 19.1; 75/386; H04N 17/02

[56] References Cited

U.S. PATENT DOCUMENTS

| | | | |
|---|---|---|---|
| 4,379,402 | 4/1983 | Harman, III | 73/23.2 |
| 5,036,251 | 7/1991 | Lee | 348/180 |
| 5,182,594 | 1/1993 | Hopson | 355/20 |
| 5,298,798 | 3/1994 | Furumiya | 348/645 |
| 5,327,228 | 7/1994 | Satyanarayana et al. | 348/647 |
| 5,402,665 | 4/1995 | Hart et al. | 73/23.2 |

Primary Examiner—James J. Groody
Assistant Examiner—Jeffrey S. Murrell
Attorney, Agent, or Firm—E. Philip Koltos

[57] ABSTRACT

A video photometric color sensing system is provided for characterizing the color of a homogeneous substance on a real time basis. The sensing system includes a sample port for holding a homogeneous substance and a camera quantifies a color video image of the homogeneous substance and provides as outputs analog voltage signals representative of the amount of red, green and blue in the color video image. A peak detector circuit receives the analog voltage signals representative of the amount of red, green and blue in the color video image and generates peak red, green and blue analog voltage signals and uses these individual voltage values of each component to derive the luminance value from software generated nonadditive matrix. Each of the peak red, green, blue and luminance analog voltage signals are converted to corresponding digital levels and then a processor compares the received red, green, blue and luminance digital levels to red, green, blue and luminance reference levels stored within the processor and indicative of known values of the homogeneous substance to determine the actual concentration of the homogeneous substance.

15 Claims, 2 Drawing Sheets

VIDEO PHOTOMETRIC COLOR SYSTEM FOR PROCESSING COLOR SPECIFIC STREAMS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

1. Field of the Invention

The present invention relates generally to a system for digitizing color video signals and, more particularly, to a system which utilizes a red/green/blue camera to detect and digitize the color hues of a homogeneous substance in order to perform an analysis, even an analyzed chemical of the homogeneous substance on a real time basis.

2. Description of the Prior Art

Real time analysis and process control of a homogeneous substance such as a metallurgical stream is presently not possible due to the lack of sensors capable of performing the required on-line analysis. Today, samples must be removed from the process stream and sent to nearby instrumentation or laboratory facilities where they are mixed with reagents and diluted before metal concentration can be discerned with typical analytical equipment such as atomic absorption spectrophotometry (AAS) or inductively-coupled plasma spectrophotometry (ICP). Only after laboratory results are obtained may process parameters be adjusted to optimize metal recovery. Ideally, an on-line instrumentation system would analyze solutions directly in-stream without dilution or other modifications.

One way to perform an on-line analytical analysis of a metallurgical stream to determine metal concentration would be to quantify a color video image of the metallurgical stream and correlate the various colors in the color image to the metal concentration. Unfortunately, although systems are presently available with gray scales to capture and retrieve color from video, none of these systems utilizes an actual color image capturing and analysis scheme. For example, frame grabbers currently available are operable to capture gray scale from video. However, frame grabbers require numerical analysis of analytical algorithms to characterize the color and are slow and processor intensive. Also, the color resolution is limited to 127 steps for the standard Y/U/V 4/1/1 format.

United States patents pertaining to video analysis are concerned with image analysis and manipulation/decoding of composite (NTSC or PAL) video signals and do not address actual color image capturing systems (see U.S. Pat. Nos. 5,212,544; 5,194,940; 5,164,998; 5,166,780; 5,146,317 and 5,031,224). U.S. Pat. No. 5,187,567 describes how this manipulation/decoding is done with filters. U.S. Pat. No. 4,797,738 describes taking a photograph of an NTSC video signal and analyzing it for color, and U.S. Pat. No. 5,150,199 describes a method for mathematically determining R/G/B color regression analysis to fit a standard color model.

As can be seen from the foregoing, although systems and processes both commercially available and described in issued U.S. patents may be utilized to perform image analysis and manipulation/decoding of composite video signals, none of these presently known systems and processes are capable of performing an on-line or real time analysis of the color video image of a homogeneous substance such as a metallurgical stream to determine metal concentration.

Consequently, there is a need for a system which is capable of quantifying a video image and analyzing the color hues or components of the video image. Such a system could be used in a metallurgical stream to determine the concentration of metal in the stream.

SUMMARY OF THE INVENTION

The present invention relates to a video photometric color sensing system designed to satisfy the aforementioned need. The video photometric color sensing system of the present invention utilizes a red/green/blue video camera to quantify an image of a metallurgical stream, and process circuitry associated with the video camera to analyze the red, green and blue components and derive the luminance value of the video image to provide an indication of the color of the stream and subsequently, for the metallurgical operation, the concentration of metallic entrained within the metallurgical stream. The system of the present invention permits an on-line, real time analysis of the metallurgical stream and this real time analysis eliminates the shortcomings of presently utilized analytical systems which all require the use of time consuming and expensive sampling and remote analysis techniques.

Accordingly, the present invention is directed to a video photometric color sensing system for characterizing the color of a homogeneous substance on a real time basis to identify the exact color of the homogeneous substance. The color sensing system includes: (a) a sample port for holding a homogeneous substance; (b) a video camera for quantifying a video image of the homogeneous substance and providing as outputs analog voltage signals representative of the amount of red, green and blue in the video image; (c) a peak detector circuit for receiving the analog voltage signals representative of the amount of red, green and blue in the video image and deriving the analog voltage signal representative of the luminance of the video image and generating peak red, green, blue and luminance analog voltage signals; (d) an analog to digital converter device for converting each of the peak red, green, blue and luminance analog voltage signals to corresponding digital levels; and (e) a processor for receiving the red, green, blue and luminance digital levels from the converter and comparing the red, green, blue and luminance digital levels to red, green, blue and luminance reference levels stored within the processor and indicative of known concentration levels of the homogeneous substance to determine the actual concentration of the homogeneous substance.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which.

DETAILED DESCRIPTION OF THE INVENTION

The present invention is directed to a video photometric color sensing system for characterizing the color of a homogeneous substance such as a metallurgical stream on a real time basis to identify the concentration of a metallic entrained in the stream. In the broadest sense, the present invention is directed to such a video photometric color sensing system which digitizes color video signals and allows a red/green/blue color camera to be used for on-line, real time analysis of the metallurgical stream in question. By using a red/green/blue camera to capture the image of a stream, the red/green/blue color and luminance values of the image may be quantified into individual voltage levels. These voltage levels are compared to a series of reference color and luminance voltage levels corresponding to the color and luminance values generated by a range of known concentrations in the metallurgical stream. When the quantified color and luminance voltage levels match a particular reference color and luminance voltage level in the range, the actual concentration of metallic in the metallurgical stream is known to be the concentration corresponding to the concentration of the particular reference color and luminance level matched. As can be appreciated, this comparison of quantified color and luminance voltage levels to reference color and luminance voltage levels provides an indication of the concentration of a particular metallic to the metallurgical stream on a real-time basis which allows the video photometric color sensing system of the present invention to be used on a non-intrusive basis. The system disclosed herein may be utilized to analyze any type of color-specific stream, such as a liquid or vapor stream, and may also be used to analyze solids.

Figure 1:
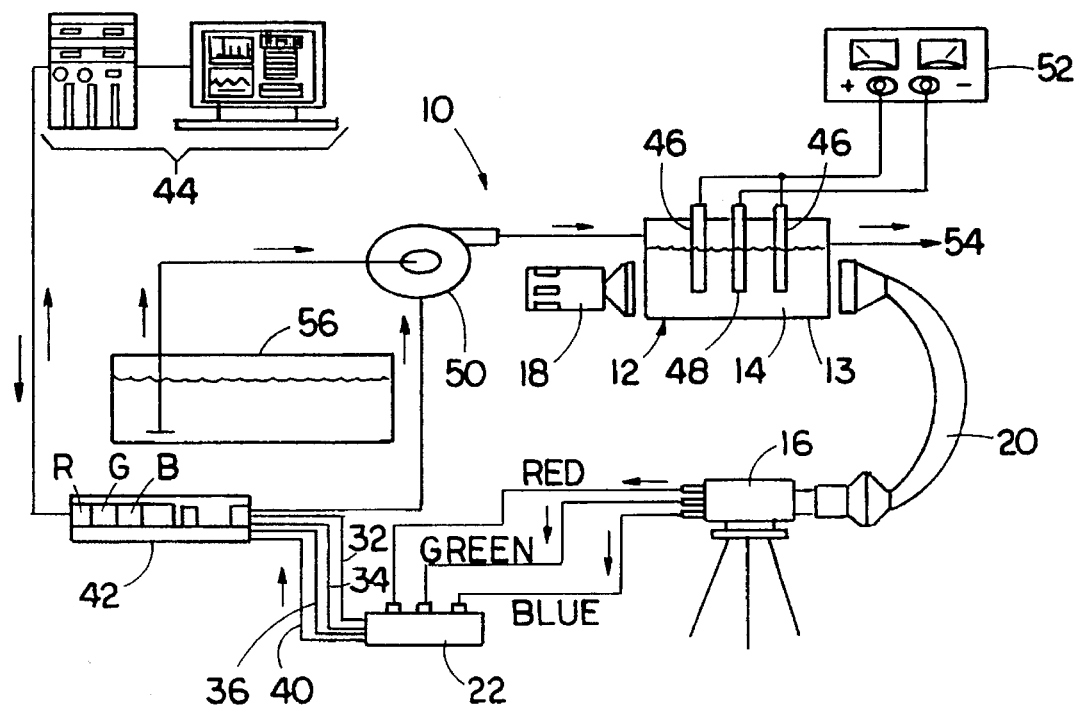
FIG. 1 is a process and component layout drawing of the video photometric color sensing system of the present invention, illustrating the various components utilized to form the system and the interconnections among the various components.

Now referring to the drawings, and particularly to FIG. 1, there is illustrated a process and component layout drawing of the video photometric color sensing system of the present invention generally designated by the numeral 10. The video photometric color sensing system 10 includes a sample port or vessel 12 for holding a homogeneous stream 14. The vessel 12 is made from a suitable translucent material to allow light to pass through the vessel wall 13. A red/green/ blue (R/G/B) camera 16 is also provided. The camera may be a Sony DXC-930 three chip R/G/B color camera or other suitable camera. As seen in FIG. 1, the camera 16 is positioned at a location remote from the vessel 12. This is done since in practice it may be difficult to position the camera 16 directly adjacent to the vessel wall 13 due to harsh industrial plant conditions. A light source 18 is positioned adjacent to the vessel wall 13 and emits light which passes through the vessel wall 13 and through the sample stream 14 held within the vessel 12. The selection of the proper light source is critical since obviously color is the essential factor in the color sensing system of the present invention. In addition, a luminance level of 100 IRE (Institute of Radio Engineers) at 125 candle power is required for proper operation of the Sony camera 16. For these reasons, the light source 18 selected for use with the camera 16 is a 3200 degree Kelvin tungsten-halogen light source.

Since the camera 16 is positioned at a location remote from the vessel 12, light emitted by the light source 18 and passed through the vessel wall 13 and homogeneous stream 14 is transferred to the camera 16 through a fiber optic cable 20. The fiber optic cable 20 is preferably made of plastic. Plastic rather than glass is selected because plastic provides a broader light representation of the visual portion of the electromagnetic spectrum.

As previously indicated, the video photometric color sensing system 10 of the present invention may be used to determine the concentration of a certain metallic entrained within a metallurgical stream. Thus, in order to determine the concentration of metallic within the metallurgical stream 14, light provided by the light source 18 passes through the vessel wall 13 and the stream 14 and is transferred via the fiber optic cable 20 to the R/G/B camera 16. The camera 16 takes a color image of the light passed through the fiber optic cable 20 and provides as outputs a "red" signal, a "green" signal and a "blue" signal each representative of the amount of red, green or blue appearing in the color image of the metallurgical stream 14. Each of the output red, green and blue signals is an analog voltage signal having a value of 0.7× the actual peak-to-peak value of the voltage generated within the camera 16. For example, if the camera 16 generates internally a 1.0 volt peak-to-peak analog voltage signal for the color red based on the quantity of red in the light received through the fiber optic cable 20, the output from the camera 16 corresponding to red will be 0.7 volt peak-to-peak. The peak-to-peak analog voltage signals corresponding to red, green and blue generated by the camera 16 are provided to a peak detector circuit designated by the numeral 22.

Figure 2:
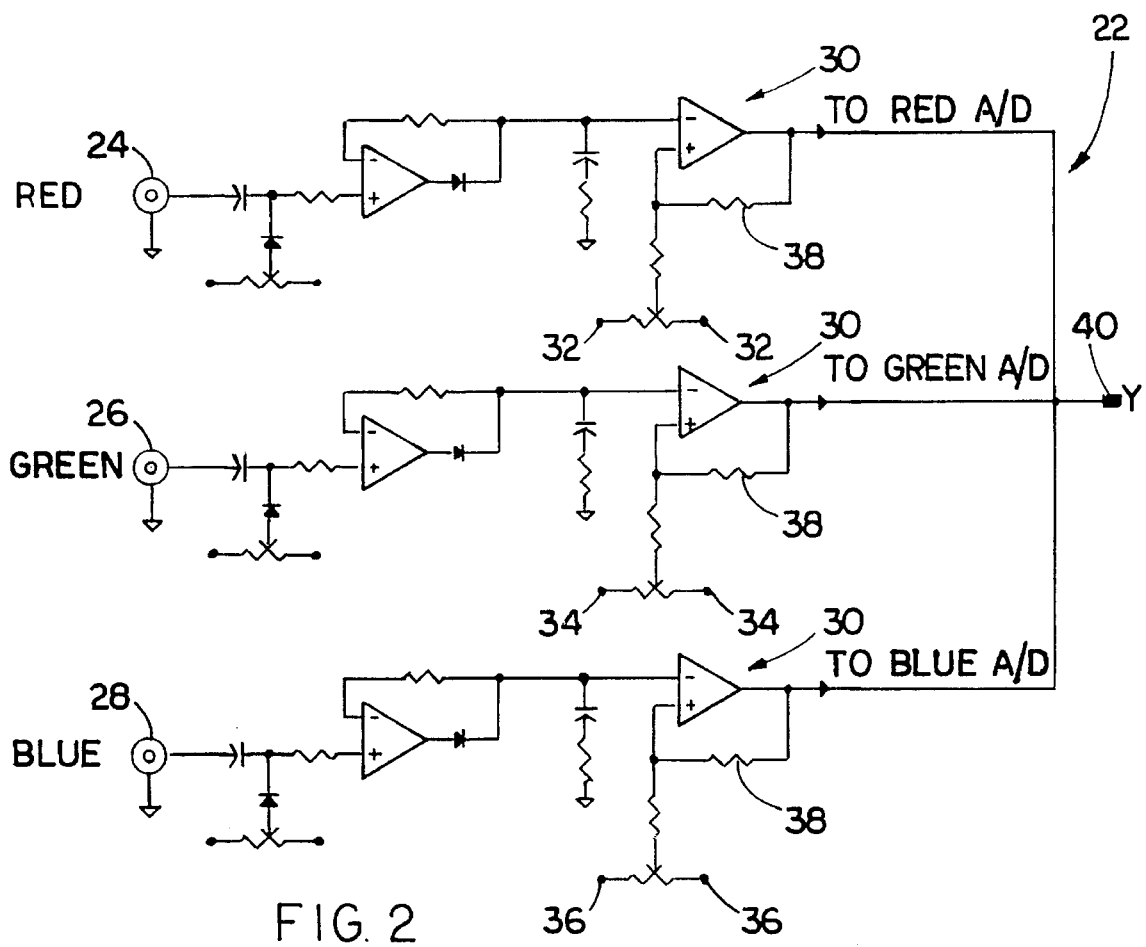
FIG. 2 is a schematic diagram of a voltage peak detector circuit which forms a portion of the video photometric color sensing system of the present invention.

As seen in FIG. 1 and more particularly in FIG. 2, the peak detector circuit 22 is designed to receive each of the red, green and blue analog voltage signals generated by the camera 16, and each of these red, green and blue analog voltage signals has a value of 0.7× the actual peak-to-peak value of the corresponding voltage generated within the camera 16. The peak detector circuit 22 is designed to provide as outputs the peak values of the received 0.7 volt peak-to-peak red, green and blue signals. In addition, the peak detector circuit 22 is also designed to provide as an output an analog voltage signal Y corresponding to the luminance value of the light received by the camera 16.

The red, green and blue analog voltage signals are provided to the peak detector circuit 22 at input nodes 24, 26 and 28, respectively. Each of the red, green and blue analog voltage signals is passed through a peak detecting circuit portion 30. Each peak detecting circuit portion 30 consists of an operational amplifier, resistor, capacitor and diode arrangement as shown. For the resistor, capacitor and diode values as indicated in FIG. 2 used with three LF 347N operational amplifiers, the peak analog voltage values of the red, green and blue color signals are provided as outputs at nodes 32, 34 and 36. In addition, the peak detector circuit 22 combines the peak analog voltage values of the red, green and blue signals each reduced across a resistor 38 to provide a peak analog voltage value of the luminance Y of the light received by the camera 16. The luminance value Y is provided as an output from the peak detector circuit 22 at node 40.

Each of the peak red, green, blue and luminance analog voltage signals 32, 34, 36 and 40 is provided to an analog to digital (A/D) converter 42. The A/D converter is conventional, and within the A/D converter 42, the peak analog voltage signals are converted to corresponding digital voltage levels. The digital voltage levels representative of the actual levels of red, green and blue within the imaged metallurgical stream, and further representative of the Y value of the imaged metallurgical stream, are provided to a processor 44. Within the processor 44 which includes a software package that incorporates a PID algorithm, these digital voltage levels are compared to a series of reference color and luminance voltage levels corresponding to the color and luminance values generated by a range of known concentrations of the certain metallic entrained in the metallurgical stream. When the quantified color and luminance voltage levels match a particular reference color and luminance voltage level in the range, the actual concentration of metallic in the metallurgical stream is known to be the concentration corresponding to the concentration of the particular reference color and luminance level matched.

As described, the video photometric color sensing system 10 of the present invention utilizes digitized analog video signals to characterize the absorptive or reflective indicators of the chrominance and luminance values of light. True R/G/B is defined as three voltage signals consisting of 0.7 volt peak-to-peak for each of the R/G/B colors provided by the camera 16. In the R/G/B video photometric color sensing system 10 described herein, color is represented as a voltage level, whereas in traditional encoded NTSC video signaling, color is represented by a phase shift referenced to NTSC color bursts. The system described herein takes the 0.7 peak-to-peak R/G/B and Y video signals at a video frame rate of 30 cycles per second and produces individual voltage levels that correspond to the R/G/B and Y peak values of the analog video signal produced by the camera 16. By converting the R/G/B and Y video information to color and luminance specific analog voltage levels, these voltage levels can then be presented to the A/D converter 42 as color and luminance specific data for processor 44-based comparison and analysis. Using this method, 70 percent of the full scale capability of the 1 volt A/D signal is utilized, providing a digital resolution of 2866 steps as contrasted to 127 steps for the NTSC system. The 2866 steps can be normalized to the full scale 4095 steps of the 12 bit A/D converter 42. Color measurements using this method were found to be very stable, deviating only ±0.0015 volt from the setpoint in 72 hours.

An example of one application of the video photometric color sensing system 10 is now given. Because copper sulfate solutions have a distinctive bluish-green color, the color sensing system 10 was utilized for the on-line analysis and control of copper in a laboratory electrolytic cell. Vessel 12 was a 1 liter copper electrolytic plating cell with the lead plates 46 as anodes and a copper slab 48 as the cathode. A metallurgical stream formed from copper in an $H_2SO_4$ solution entered the vessel 12 using a peristaltic pump 50 with a 4 to 20 ma interface to the A/D converter 42. A DC power supply 52 provided the needed current density to deposit copper on the cathode.

On-line analysis was performed near the outlet 54 of the vessel 12 by connecting the fiber optic cable 20 from the camera 16 to the vessel 12. Color came through the fiber optic cable 20 to the camera 16 when the equipment was activated and the light source 18 was turned on. The circuitry described with respect to FIGS. 1 and 2 was operated to digitize the color images seen by the camera 16 and these digitized values were used to control the operation of the pump 50 and thus the flow rate of the metallurgical stream from the storage vessel 56 to the vessel 12, and from the vessel 12 to the exit stream 54.

In this example, the processor 44 received the digital levels of the red, green, blue and Y signals from the A/D converter 42 and compared these received levels to a set of reference levels stored within the processor 44 corresponding to the color and luminance values generated by a known concentration of a copper within a $H_2SO_4$ solution. When the quantified color and luminance digital levels approached the reference color and luminance voltage levels, this provided an indication that most of the copper had been removed from the solution and deposited on the cathode 48. At this point, the processor 44 through its software package then provided a digital signal to the A/D converter 42 which in turn due to the particular software provided as an output an analog current signal to the pump 50 to introduce more solution into the vessel 12. As can be appreciated from this example, the comparison of quantified color and luminance digital levels to reference color and luminance voltage levels provides an indication of the concentration of copper in solution on a real-time basis which allowed solution to be transferred from the vessel 56 to the vessel 12 without shutting the system down and performing a time-consuming analysis.

Figure 3:
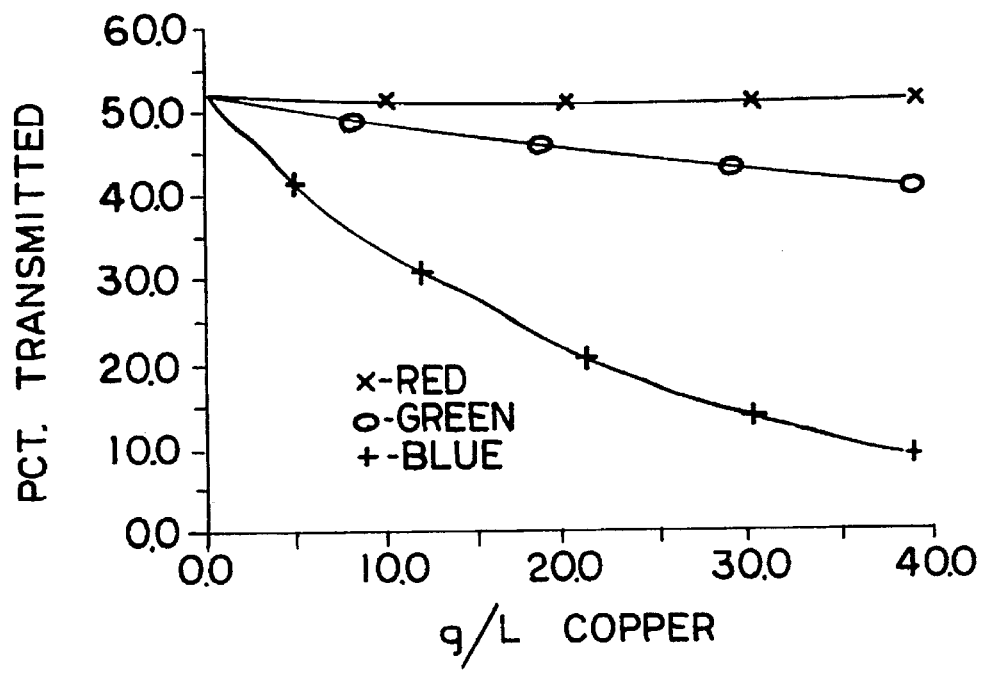
FIG. 3 is a graphic illustration of the various colors observed in a test solution subjected to an analysis utilizing the video photometric color sensing system of the present invention.

Color measurements were calibrated to specific copper concentrations by preparing solutions with varying concentrations of copper sulfate and $H_2SO_4$. FIG. 3 shows the digitized readings of the red, green and blue signals obtained as copper concentration varied. As seen in FIG. 3, the red signal is the most indicative of the copper color over a wide concentration range (0.1 to 40 g/L Cu). This would be expected because bluish-green solution absorbs light in the red region of the electromagnetic spectrum. With the information given in FIG. 3, a specific copper concentration was selected as the control setpoint by using the corresponding red signal.

Figure 4:
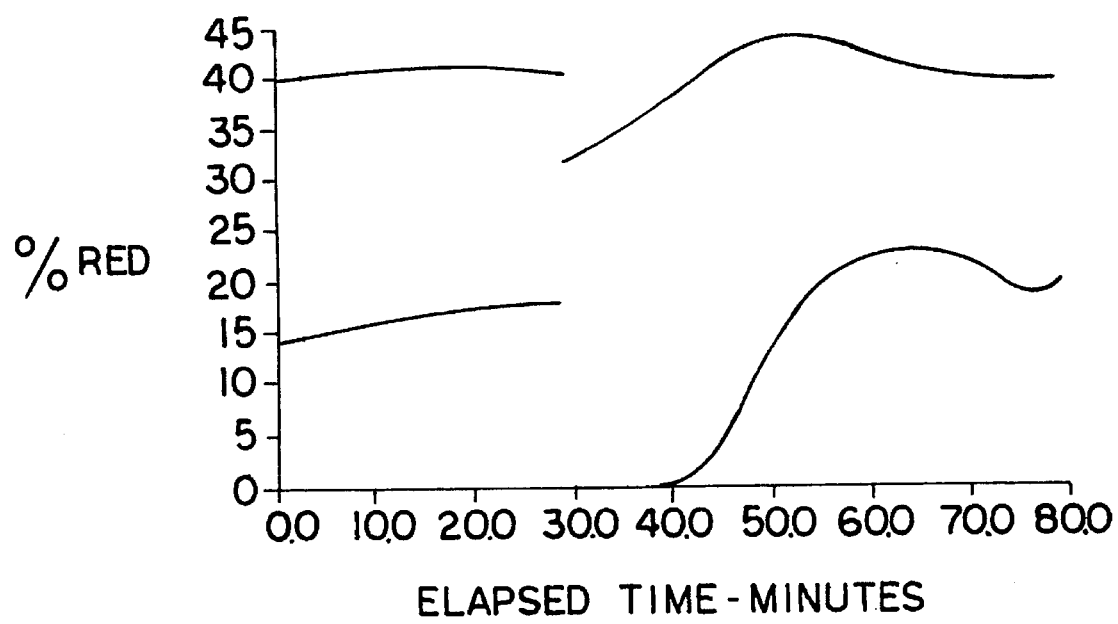
FIG. 4 is a graphic illustration depicting how the video photometric color sensing system of the present invention is utilized to control the amount of copper removed from a copper-containing metallurgical stream.

To test process control of the copper circuit, a solution containing 6.0 g/L Cu and 185 g/L $H_2SO_4$ was placed in the vessel 12. The control point was set at 6.0 g/L Cu and plating was initiated. FIG. 4 shows how quickly steady state was attained. Random samples were taken during the run to compare the copper reading from this system with atomic absorption analysis. All results were within ±0.3 g/L Cu. To see how well the system 10 would handle a disturbance, a solution of 40 g/L Cu was poured directly into the vessel 12 twenty nine minutes into the run to increase the copper concentration to 12.0 g/L. FIG. 4 shows how control quickly restored the system to steady state.

It is thought that the present invention and many of its attendant advantages will be understood from the foregoing description and it will be apparent that various changes may be made in the form, construction and arrangement of the parts of the invention described herein without departing from the spirit and scope of the invention or sacrificing all of its material advantages, the form hereinbefore described being merely a preferred or exemplary embodiment thereof.

We claim:

1. A video photometric color sensing system for characterizing the color of a homogeneous substance on a real time basis, comprising:

(a) a sample port for holding a homogeneous substance;

(b) camera means for quantifying a color video image of said homogeneous substance and providing as outputs analog voltage signals representative of the amount of red, green and blue in said color video image;

(c) peak detector circuit means for receiving said analog voltage signals representative of the amount of red, green and blue in said color video image and generating peak red, green and blue analog voltage signals and for using the individual voltage values of each red, green and blue component to derive the luminance value from software generated nonadditive matrix;

(d) converter means for converting each of said peak red, green and blue analog voltage signals and said luminance value to corresponding digital levels; and (e) processor means for receiving said red, green, blue and luminance digital levels from said converter means and comparing said received red, green, blue and luminance digital levels to red, green, blue and luminance reference levels stored within said processor means to determine the actual concentration of said homogeneous substance.

2. The video photometric color system as recited in claim 1, wherein:

said sample port is made from a translucent material to allow light to pass therethrough; and said sample port is illuminated by a light source positioned to allow the light it generates to pass through said sample port and through said homogeneous substance contained therein towards said camera means.

3. The video photometric color system as recited in claim 2, wherein said light source is a 3200 degree K. halogen lamp.

4. The video photometric color system as recited in claim 3, further comprising:

fiber optic means extending between said sample port and said camera means to transfer light passing through said sample port and through said homogeneous substance to said camera means.

5. The video photometric color system as recited in claim 4, wherein said fiber optic means is made of plastic.

6. The video photometric color system as recited in claim 1, wherein said homogeneous substance is a liquid.

7. The video photometric color system as recited in claim 1, wherein said homogeneous substance is a solid.

8. The video photometric color system as recited in claim 1, wherein said homogeneous substance is a vapor.

9. A video photometric color sensing system for characterizing the color of a homogeneous substance by controlling the rate of color change of said homogeneous substance, comprising:

(a) a process stream of said homogeneous substance;

(b) a sample port for receiving a sample stream from said homogeneous process stream;

(c) equipment means for increasing or decreasing the color hue of said homogeneous process stream;

(d) camera means for quantifying a color video image of said homogeneous substance within said sample port and providing as outputs analog voltage signals representative of the amount of red, green and blue in said color video image;

(e) peak detector circuit means for receiving said analog voltage signals representative of the amount of red, green and blue in said color video image and generating peak red, green and blue analog voltage signals and for using the individual voltage values of each red, green and blue component to derive the luminance value from software generated nonadditive matrix;

(f) converter means for converting each of said peak red, green and blue analog voltage signals and said luminance value to corresponding digital levels; and (g) processor means for receiving said red, green, blue and luminance digital levels from said converter means and comparing said received red, green, blue and luminance digital levels to red, green, blue and luminance reference levels stored within said processor means to determine the actual concentration of said homogeneous substance within said sample port;

said processor means providing an operating signal to said converter means which in turn is transmitted to said equipment means when said actual color of said homogeneous process stream does not match the preselected desired level of color of said homogeneous process stream.

10. The video photometric color system as recited in claim 9, wherein:

said sample port is made from a translucent material to allow light to pass therethrough; and said sample port is illuminated by a light source positioned to allow the light it generates to pass through said sample port and through said homogeneous substance contained therein towards said camera means.

11. The video photometric color system as recited in claim 10, wherein said light source is a 3200 degree K. halogen lamp.

12. The video photometric color system as recited in claim 11, further comprising:

fiber optic means extending between said sample port and said camera means to transfer light passing through said sample port and through said homogeneous substance to said camera means.

13. The video photometric color system as recited in claim 12, wherein said fiber optic means is made of plastic.

14. The video photometric color system as recited in claim 9, wherein said homogeneous substance contains metals and said substance increases in color hue as the metal concentration increases.

15. The video photometric color system as recited in claim 9, wherein said equipment means includes a plating power supply and a pump for transferring said process stream through said sample port.

* * * * *